United States Patent [19]
Hall

[11] Patent Number: 5,131,846
[45] Date of Patent: Jul. 21, 1992

[54] PROPHY CUP SHIELD

[76] Inventor: Roger A. Hall, 4308 Dalton Pk., SE., Cleveland, Tenn. 37323

[21] Appl. No.: 821,450

[22] Filed: Jan. 16, 1992

[51] Int. Cl.⁵ ................................................ A61C 1/16
[52] U.S. Cl. .................................... 433/116; 433/125; 433/166
[58] Field of Search ..................... 433/116, 125, 166

[56] References Cited

U.S. PATENT DOCUMENTS

| | | | |
|---|---|---|---|
| 2,943,343 | 7/1960 | Jankelson | 433/166 |
| 4,259,071 | 3/1981 | Warden et al. | 433/166 |
| 4,424,036 | 1/1984 | Lokken | 433/116 |

Primary Examiner—John J. Wilson
Attorney, Agent, or Firm—Gregory J. Gore

[57] ABSTRACT

A prophy cup shield is cylindrical in shape and attaches to a dental handpiece by way of elastic fit around the nose of the handpiece. The inside of the shield includes novel spiral tracks which cooperate with the rotating cup to force any trapped paste that may find its way between the cup and the shield back out over the rim of the rotating cup. The shield prevents the splatter of cleaning paste and patient bodily fluids. The shield also prevents against accidental injury to the patient's gum because when in use the shield extends beyond the circumferential rim of the rotating cup.

5 Claims, 1 Drawing Sheet

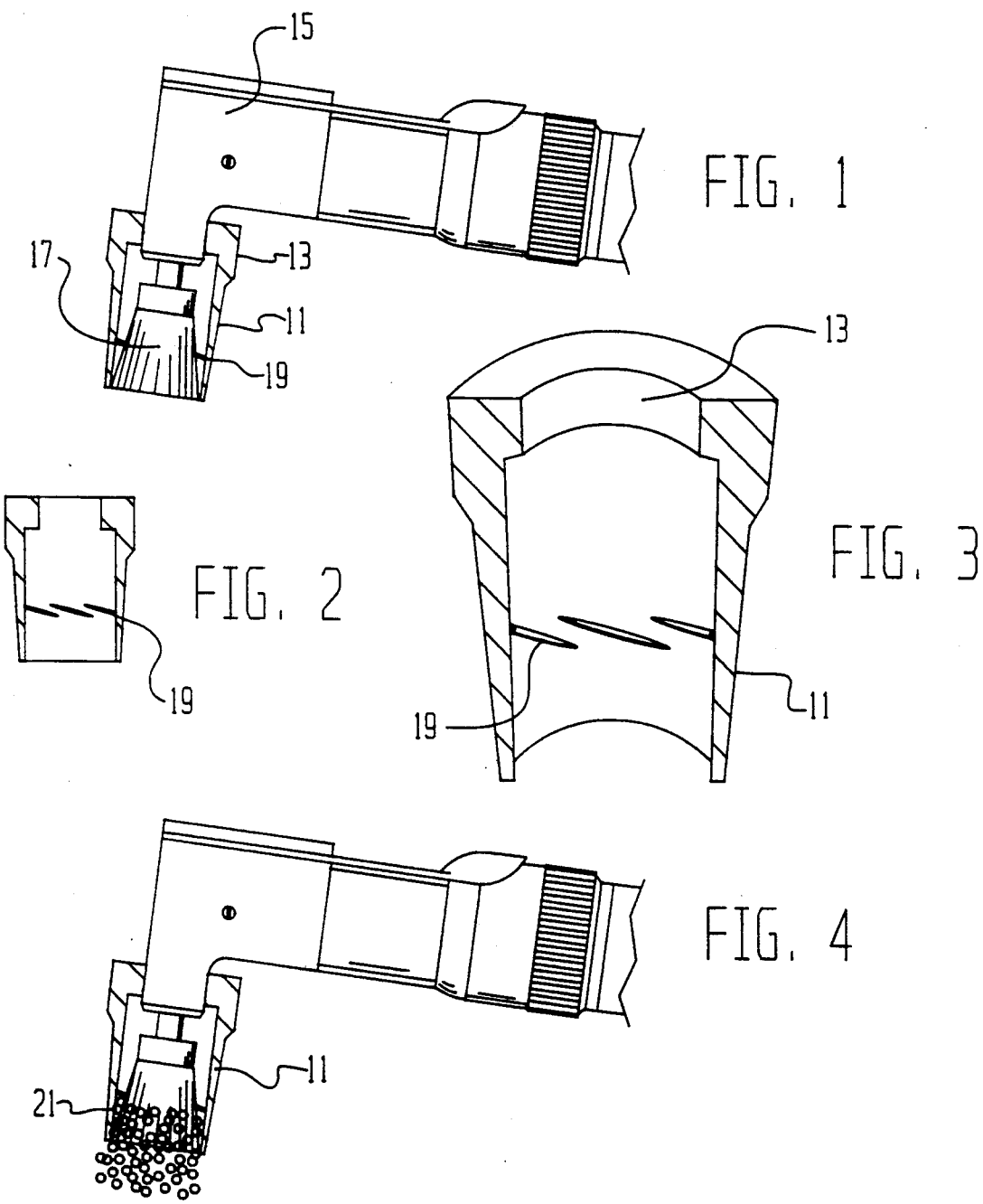

PROPHY CUP SHIELD

FIELD OF THE INVENTION

This invention relates to tooth cleaning devices utilized by the dental profession and more specifically to the power-driven handpieces and polishing cups used with an abrasive compound for cleaning teeth.

BACKGROUND OF THE INVENTION AND PRIOR ART

The modern dental tooth cleaning procedure is perhaps the most commonly performed procedure in dentistry. Teeth are cleaned by the practitioner by way of a power-driven rotary flexible rubber cup, which contains a quantity of slightly abrasive tooth cleaning paste.

A problem in the art exists with the cleaning paste being thrown off by centrifugal force of the rotating cup. The cleaning cups, more commonly called "prophy cups", which are approximately 6 millimeters in diameters, may rotate at speeds of up to 5,000 RPM. Not only can the paste be thrown from the cup during the procedure, but also saliva and patient blood can likewise splatter. With the advent of concern of containment and protection from sharing bodily fluids in dentistry, there is a need in the art for an effective method of controlling and isolating this splatter of cleaning paste and patient body fluids.

In the past, flexible covers have been used to protect against prophy cup splatter. These shields were fitted on the end of the right-angle handpiece customarily used to drive the prophy cup with the shield remaining stationary while the power-driven cup rotated within the sleeve. This shield reduced splatter, but prior art shields trapped paste between the inner wall of the shield and the rotating cup. Cleaning paste forced into this area wastes paste and the trapped paste can adversely effect the shaft and bearing assembly of the handpiece. The present invention provides a prophy cup shield which solves this problem.

The closest prior art of which the applicant is aware is U.S. Pat. No. 2,943,343 to B. Jankelson, issued Jul. 5, 1960; and U.S. Pat. No. 1,834,726 to W. W. Ozon, issued Dec. 1, 1931. Both of these references show the concept of a prophy shield and therefore are pertinent, but neither teaches or suggests the present invention.

SUMMARY OF THE INVENTION

A unique prophy cup shield has been devised which functions as a cylindrical covering shield that attaches to the dental handpiece by way of elastic fit around the nose of the handpiece. The inside of the shield includes novel spiral tracks which cooperate with the rotating cup to force any trapped paste that may find its way between the cup and the sleeve back out over the rim of the rotating cup. Therefore, the area between the shield and the cup remains free from trapped paste.

It has also been found that the present invention protects against accidental injury to the patient's gum by interposing the shield material around the circumferential rim of the rotating cup. The portion of the shield in this area therefore acts as a shield when cleaning areas of the tooth close to the patient's gum line. Further objects and advantages of the present invention will be apparent from the following drawings and description of the preferred embodiment.

BRIEF DESCRIPTION OF THE DRAWINGS

FIG. 1 is a side sectional view of the present prophy cup shield affixed to the nose of the dental handpiece.

FIG. 2 is a side sectional view of the shield.

FIG. 3 is a top front sectional view.

FIG. 4 is a side sectional view showing the action of the spiral tracks against the cleaning paste.

DESCRIPTION OF THE PREFERRED EMBODIMENT

Referring now to FIG. 1, the shield 11 includes a sleeve portion 13 at the top which fits over the nose of handpiece 15. The shield of the present invention surrounds the cup. It is not necessary that the shield extend beyond the end of the cup and good results have been found if the shield is the same length or even ½-millimeter shorter than the rotating cup. The shield is preferably made of elastomeric material, such as molded latex or vinyl rubber. The sleeve is dimensioned to have a diameter smaller than that of the nose of the handpiece so that when fitted on the handpiece, the shield is attached firmly by an elastic frictional grip. As shown in this figure, the free end of the shield closely fits around the rim of prophy cup 17 which is even with or extends approximately ½-millimeter from the end of the shield when it is properly fitted.

FIG. 2 shows greater detail of spiral tracks 19. In one embodiment of the invention, six tracks are used around the circumference of the inner wall of the shield and are angled at approximately 10-degrees. The tracks extend radially inward to a point where they contact the circumference of the prophy cup as more clearly seen in FIG. 1. Referring to FIG. 3, greater detail of the shape of the tracks and their location is shown.

Referring now to FIG. 4, a quantity of paste 21 is shown trapped between the prophy cup and the shield 11. Because the prophy cup and the shield are made of elastomeric materials, they both can be deformed when pressed against the human tooth during the cleaning procedure. This deformation, together with application pressure of the paste, can cause the paste to pack into the shield. With the present invention, however, any paste that may find its way behind the wiper tracks due to deformation of the shield is soon thrown downward back over the rim of the rotating prophy cup due to the interaction with the spiral tracks. The spiral tracks act as wipers to block trapped paste from entering the area around the prophy cup shaft and handpiece bearing assembly.

The angled tracks function in this manner because the trapped paste rotates within the shield since it is more adherent to the external surface of the prophy cup than the inner surface of the shield. When the rotating paste hits the inclined tracks, it is thrown downward toward the end of the prophy cup. It is, therefore, important to the operation of the present invention that the surface of the inner wall of the shield be less adherent to the paste than the outside circumference of the cup. With this selection of materials, the paste is constantly moving within the shield, rather than stationary with the cup rotating in the center of a quantity of stationary trapped paste. To facilitate the operation of the present shield, a non-stick coating, such as Teflon(R), may be applied to the surface of its inner wall and likewise to the spiral tracks.

It should be understood that the above description discloses specific embodiments of the present invention and are for purposes of illustration only. There may be other modifications and changes obvious to those of ordinary skill in the art which fall within the scope of the present invention which should be limited only by the following claims and their legal equivalents.

What is claimed is:

1. A shield for a powered dental handpiece with a rotary cleaning cup, comprising:

a dental handpiece having a nose portion fitted with a rotary cleaning cup;

an anti-splatter shield fitted to the nose of said handpiece and entirely surrounding the cleaning cup; and the shield including one or more radial projections on its inner wall along its circumference between the shield and the cup to prevent the axial movement of cleaning paste into the area inside of the shield adjacent the nose of the handpiece.

2. The dental handpiece shield of claim 1 wherein the radially extending portions includes a plurality of spiral tracks extending inwardly and contacting said cleaning cup.

3. The dental handpiece shield of claim 2 further including an elastomeric sleeve portion which resiliently grips the nose of the handpiece.

4. The dental handpiece shield of claim 3 wherein the shield is molded of latex rubber or similar elastomeric substance.

5. The dental handpiece shield of claim 4 further described in that the inner wall of said shield is coated with an anti-stick material or of a material which has a naturally occurring anti-stick surface.

* * * * *